United States Patent [19]

Takemoto et al.

[11] 4,127,125
[45] Nov. 28, 1978

[54] DEVICES FOR TRANSMITTING ULTRASONIC WAVES TO TEETH

[75] Inventors: Kiyochika Takemoto, Kodaira; Yasuo Suzuki, Kurume; Yoshihito Ochiai, Fujisawa; Syozi Nakashima, Ninomiya; Midori Hayashi, Yamakita, all of Japan

[73] Assignees: Lion Hamigaki Kabushiki Kaisha; Kaijo Denki Kabushiki Kaisha, both of Japan

[21] Appl. No.: 752,894

[22] Filed: Dec. 21, 1976

[30] Foreign Application Priority Data

Dec. 22, 1975 [JP] Japan .................... 50/153085
Mar. 24, 1976 [JP] Japan .................... 51/35363[U]

[51] Int. Cl.² .................... A61C 19/06; A61M 31/00
[52] U.S. Cl. .................... 128/172.1; 128/24 A; 32/40 R; 32/DIG. 4
[58] Field of Search ............ 128/172.1, 24 A, 62 A, 128/409, 136; 32/40 R, DIG. 4, 58

[56] References Cited

U.S. PATENT DOCUMENTS

| | | | |
|---|---|---|---|
| 2,789,557 | 4/1957 | Davis, Jr. | 128/24 A |
| 3,060,935 | 10/1962 | Riddell | 128/136 X |
| 3,234,942 | 2/1966 | Simon | 128/172.1 |
| 3,371,660 | 3/1968 | Carlin | 128/24 A X |
| 3,380,446 | 4/1968 | Martin | 128/172.1 X |
| 3,401,690 | 9/1968 | Martin | 128/172.1 |
| 3,847,662 | 11/1974 | Massa | 128/24 A X |

*Primary Examiner*—Lee S. Cohen
*Attorney, Agent, or Firm*—Steinberg & Blake

[57] ABSTRACT

For the purpose of forming a reinforcing layer of a decay-retarding agent on the surface of teeth, a device is provided for transmitting ultrasonic waves to the teeth while the latter are in contact with a decay-retarding agent. The device includes an enclosure which is adapted to contain a medium for transmitting ultrasonic waves, this enclosure including a sheet material which defines a hollow interior space in which an ultrasonic wave transmitting medium is adapted to be located. This sheet material of the enclosure has the property of being impermeable to the ultrasonic wave transmitting medium, so that the latter cannot pass through the sheet material. In addition, the sheet material has the property of transmitting ultrasonic waves therethrough. Thus, when a part of the sheet material is situated in the immediate vicinity of a tooth in contact with a decay-retarding agent which also engages the tooth, ultrasonic waves can be transmitted through the medium and through the sheet material so as to act on the decay-retarding agent and the teeth to form thereon a reinforcing layer of the decay-retarding agent.

15 Claims, 17 Drawing Figures

DEVICES FOR TRANSMITTING ULTRASONIC WAVES TO TEETH

BACKGROUND OF THE INVENTION

The present invention relates to a device for forming a reinforcing layer of a decay-retarding agent on the surface of a tooth by exposing the latter to ultrasonic waves in the presence of a decay-retarding agent.

In order to retard tooth decay, it is known to manually coat the surface of the tooth with a decay-retarding agent such as tin fluoride, sodium fluoride, or fluoroamine. However, if reliance is made only on such a coating to retard tooth decay, the results are not satisfactory inasmuch as such a coating has only a poor capability of adhering to a tooth and is dissolved away in a relatively short time. Thus, with such procedures it is impossible to achieve a lasting effect for the decay-retarding agent. Furthermore, even while a coating of a decay-retarding agent remains on the surface of a tooth, the capability of preventing calcium from dissolving out from the tooth surface is extremely poor.

Since the method for forming a reinforcing layer of a decay-retarding agent on the surface of a tooth by radiation of ultrasonic waves in the presence of the decay-retarding agent is based on the novel finding, there has not been known a suitable device or tool for practising this method appropriately.

Some of us has already proposed a method in which a ultrasonic vibrator as a ultrasonic wave-generating member is disposed in a tray having a U-shaped section, a tooth decay-retarding agent is coated in advance on the surface of a tooth to be treated, the tray is capped on the coated tooth, and then ultrasonic waves are radiated to effect the treatment. According to this method, however, if a ultrasonic wave transmitting medium is not filled between the vibrator and the tooth, ultrasonic waves are not transmitted effectively. Accordingly, the treatment has heretofore been conducted while water or the like is kept in the mouth. However, this is very troublesome and the method is not practical. Moreover, the tooth decay-retarding agent is wastefully leaked out during the treatment.

SUMMARY OF THE INVENTION

It is therefore a primary object of the present invention to provide a device for the tooth decay-retarding treatment using ultrasonic waves in which the foregoing defects involved in the conventional method are overcome by disposing a ultrasonic wave transmitting medium-containing vessel between a tooth decay retarding agent contacted with the surface of a tooth and a ultrasonic vibrator, and in which by disposition of the above-mentioned vessel, a broad area of the tooth surface can easily be treated effectively at one time and by the presence of the ultrasonic wave transmitting medium always filled between the ultrasonic wave vibrator and a tooth to be treated, ultrasonic waves can be effectively transmitted and scattering and leakage of the tooth decay-retarding agent can be prevented.

A secondary object of the present invention is to provide a device for the tooth decay-retarding treatment in which by forming a communicating passage in a vessel capable of being disposed between a tooth decay-retarding agent contacted with the tooth surface and a ultrasonic vibrator so that the inside and outside of said vessel are communicated with each other through said communicating passage, breathing through the oral cavity is made possible even during the treatment and it is made possible to dispose a saliva tube according to need, whereby the treating operation can be performed without giving pains to a patient.

In accordance with the present invention, these objects and other objects and advantages can be attained by a device to be disposed between a tooth decay-retarding agent contacted with the tooth surface and a ultrasonic vibrator for forming a reinforcing layer of the decay-retarding agent on the tooth surface by irradiation of ultrasonic waves, which includes a hollow portion for containing therein a ultrasonic wave transmitting medium and an enclosure surrounding said hollow portion, said enclosure being composed of a material allowing transmission of ultrasonic waves but not allowing permeation of the ultrasonic wave transmitting medium.

BRIEF DESCRIPTION OF THE DRAWINGS

FIGS. 8, 9, 10, 11-(a) and 11-(b) are views illustrating various examples of the section taken along the line II—II of FIG. 7.

DETAILED DESCRIPTION OF THE PREFERRED EMBODIMENTS

Embodiments of the present invention will now be described in detail by reference to the accompanying drawings.

Some of us have already proposed to treat teeth in such a way that ultrasonic waves are applied to a surface of a tooth in the presence of a decay-retarding agent so as to form a reinforcing covering layer of the decay-retarding agent on the surface of the tooth. The effects which are achieved by way of such a procedure are illustrated in FIGS. 1 and 2 which clearly show the excellent results achieved by such a procedure with respect to preventing dissolving out of calcium and reinforcing the tooth surface by strengthening the same.

Figure 1:
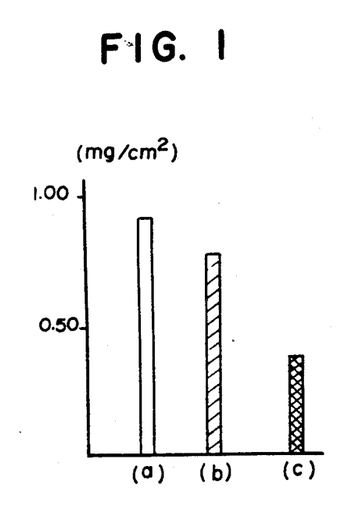
FIGS. 1 and 2 are graphs illustrating the effects of the tooth decay-retarding treatment utilizing ultrasonic waves while comparing it with the non-treatment and the manual coating of a fluorine-containing tooth retarding agent.

Referring specifically to FIG. 1 the graph shown therein indicates the amounts od $Ca^{++}$ dissolved out of different samples. It will be noted that FIG. 1 shows three different amounts of such calcium ions dissolved out of teeth. The amount (a) was dissolved out of an untreated cut human tooth. The amount (b) was dissolved out of a cut human tooth which had been dipped in an 8% $SnF_2$ solution for 5 minutes. The amount (c) was dissolved out of a cut human tooth which had been exposed to ultrasonic vibrations having a frequency of 19 KHz while the sample was dipped in an 8% $SnF_2$ for 3 minutes.

After the above treatments which resulted in the amounts (b) and (c) of FIG. 1, the samples treated in this way together with the untreated sample having the amount (a) were dipped in a buffer solution containing 0.1 mole/l of acetic acid at 37° C. for 5 hours.

Figure 2:
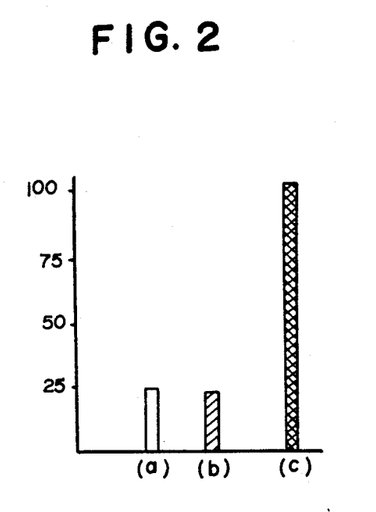

FIG. 2 is a graph showing the Vickers hardness of the above samples which gave the amounts shown in FIG. 1. The Vickers hardness shown in FIG. 2 was measured after the samples had been dipped in the 0.1 mole/l buffer solution of acetic acid for 5 hours for the purpose of effecting deliming.

Figure 3:
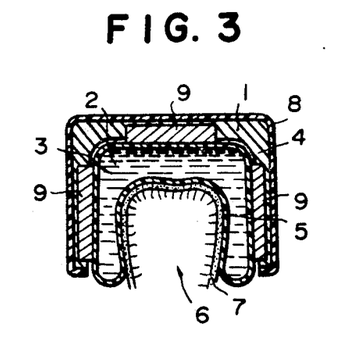
FIG. 3 is a sectional view showing an embodiment of the treatment in which the device of the present invention is used.

Referring now to FIG. 3, the vessel 1 of the present invention has a hollow portion 3 containing therein a ultrasonic wave transmitting medium 2, and an enclosure 4 surrounding the hollow portion 3 is composed of a material allowing transmission of ultrasonic waves but not allowing permeation of the ultrasonic wave transmitting medium 2. A groove 5 covering a tooth 6 is formed on the vessel 1.

A fluid except a gas may be contained as the ultrasonic wave transmitting medium 2 in the hollow portion 3. For example, an oil such as silicone oil, water such as degasified water and a pasty highly viscous fluid can be used. As the material constituting enclosure 4 surrounding the hollow portion 3, there may be employed materials allowing transmission of ultrasonic waves but not allowing permeation of the ultrasonic wave transmitting medium 2, such as plastic materials, thin stainless steel, rubbery films and aluminum foils.

Referring to FIG. 3, the surface of the tooth 6 is coated in advance with a tooth decay-retarding agent 7 such as a pasty agent containing tin fluoride, sodium fluoride or fluoroamine as an active ingredient. A plurality of ultrasonic vibrators 9 are mounted on the inner surface of a tray 8 having a U-shaped section.

Figure 4:
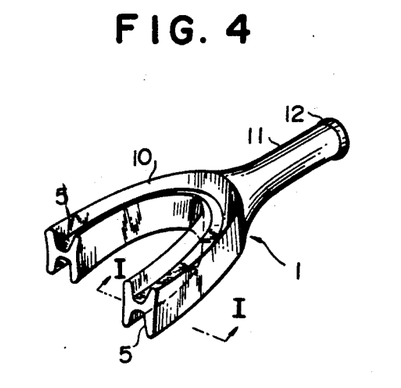
FIG. 4 is a perspective view showing another embodiment of the treatment in which the device of the present invention is used.

When the tooth decay-retarding treatment is conducted, the vessel 1 is capped on the tooth 6 coated with the tooth decay-retarding agent 7, and the tray 8 was further capped on the vessel 1 to contact the inside and outside of the vessel 1 closely with the tooth 6 and the vibrators 9, respectively. If the vibrators 9 are ultrasonically oscillated in this state, ultrasonic waves arrive at the surface of the tooth 6 assuredly through the medium 2 in the vessel 1 and a reinforcing layer of the decay-retarding agent 7 is effectively formed in the surface portion of the tooth 6. Since the medium 2 is always intervened between the vibrators 9 and the surface of the tooth 6, ultrasonic waves generated are completely transmitted, and since the decay-retarding agent 7 is pressed by the vessel 1, scattering of the decay-retarding agent can be prevented. Accordingly, the treatment effect can be insured and wasteful consumption of the decay-retarding agent can be prevented. It is possible to coat the decay-retarding agent in advance on the inner surface of the vessel 1. When a soft and flexible material is chosen as the material constituting the vessel 1, a good compatibility is attained between the tooth 6 and the vibrators 9 and transmission of ultrasonic waves is improved. The vessel 1 may have a shape or area covering a part of the tooth row or may be formed to cover all the tooth row as shown in FIG. 4. The shape or area of the vessel 1 is appropriately chosen depending on the kinds and number of teeth to be treated.

Figure 5:
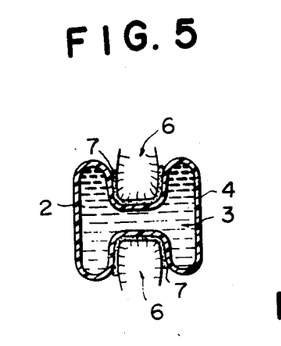
FIG. 5 is a view showing the section taken along the line I—I of FIG. 4.
Figure 6:
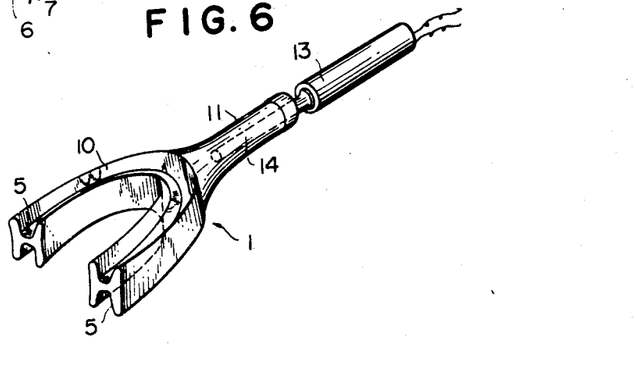
FIG. 6 is a perspective view illustrating an embodiment in which a ultrasonic vibrator is attached to the device of the present invention.

In another embodiment shown in FIGS. 4 and 5, the vessel 1 has a horseshoe portion 10 and a handle portion 11, and the horseshoe portion 10 has a groove 5 and an H-shaped section hollow portion while the handle portion 11 has a round section hollow portion. Both hollow portions of the horseshoe portion 10 and the handle portion 11 are communicated with each other to form a hollow portion 3 as a whole. A ultrasonic wave transmitting medium 2 such as degasified water or a silicone oil is filled in this hollow portion 3.

A seal 12 is disposed to prevent leakage of the ultrasonic wave transmitting medium 2 contained in the hollow portion 3 of the vessel 1. The seal 12 is composed of a relatively soft, flexible and film-like material having some self-restoring property. This is, for example, selected from such materials as aluminum foil, natural and synthetic resin, laminated materials with aluminum foil and synthetic resin, aluminum foil and paper, synthetic resin and paper, and also above materials further treated with wax. This seal 12 is attached to the vessel 1 after or before filling of the medium 2 according to a known method.

Further, an outer portion of the seal 12 may be composed of different materials from its inner portion. For example, by using such flexible film-like materials as rubber, silicon rubber, saran, polyvinyl-alcohol in the outer portion, and the above-mentioned materials in the inner portion, when a horn 14 of a ultrasonic vibrator 13 is inserted into the hollow portion 3 of the vessel 1 while breaking through the inner portion of the seal 12, as is mentioned later, leakage of the medium 2 from the hollow portion 3 through the clearance between the horn 14 and the outer portion of the seal 12 can be reduced to a minimum level. An enclosure 4 of the horseshoe portion 10 is composed of the same material as mentioned above with respect to the embodiment shown in FIG. 3.

In the present invention, since the horseshoe portion of the vessel is formed to have an H-shaped section, the upper and lower grooves 5 can be simultaneously fitted on the upper and lower tooth rows. Of course, in this embodiment, the horseshoe portion may be formed to have a U-shaped section so as to treat one of the upper and lower tooth rows.

Since the enclosure 4 of the horseshoe portion 10 is composed of a relatively soft, flexible plastic material or aluminum foil or thin stainless steel having a good ultrasonic wave transmitting property, if the vessel 1 is placed on the tooth row and it is lightly bitten, the surface of the vessel 1 is closely contacted with the tooth 6 as shown in FIG. 5. Then, a horn of of an ultrasonic vibrator 13 causing in the hollow tubular shaft portion 11 vertical vibrations or vibrations perpendicular to the axis of the tubular portion 11 is inserted into the hollow portion 3 of the vessel 1 while breaking through the seal 12, so that ultrasonic vibrations are directly transmitted to the medium 2. Since the seal 12 is formed of a film of a material having the above-mentioned properties, leakage of the medium 2 from the hollow portion 3 through the clearance between the horn 14 and the broken seal 12 can be reduced to a minimum level. Even by contacting the horn 14 with the outer portion of the seal 12 formed on the end of the handle portion 11 without inserting it into the hollow portion 3 of the vessel 1, ultrasonic waves can be transmitted to the medium 2. The tooth decay-retarding agent may be coated in advance on the surface of a tooth to be treated or the inner surface of the groove 5 of the horseshoe portion 10. In practising the present invention, it is preferred that the decay retarding agent 7 be liquid or pasty. If the ultrasonic vibrator 13 is actuated in the above-mentioned state, ultrasonic vibrations of the horn 14 are transmitted to the medium 2 contained in the hollow portion 3 of the horseshoe portion 10 and then transmitted to the tooth 6 through the retarding agent 7 held between the groove 5 and the tooth 6, whereby the decay-retarding agent 7 is impregnated into the surface portion of the tooth 6 to form a reinforcing layer having a strong durability in the surface portion of the tooth 6. When the device of the present embodiment is used, teeth in a relatively broad region of both the upper and lower tooth rows can be treated at one time. Further, the device per se can be handled and attached very easily and since the groove 5 is closely contacted with the tooth surface, irradiation of ultrasonic waves can be performed assuredly. Moreover, since the liquid or pasty decay-retarding agent 7 is held between the groove 5 and the tooth 6, the effect of the agent 7 is insured and scattering thereof is effectively prevented. Still further, since the ultrasonic vibrator 13 is disposed outside the oral cavity, a lead wire need not be put into the oral cavity and the safety of the treatment can be enhanced.

By experiments made by use in connection with the above tooth treatment, especially with respect to the treating effect and the frequency of ultrasonic waves, it was confirmed that the treatment effect is high at a relatively low frequency and good results are obtained when the frequency is not higher than 500 KHz. It also was found that especially good results are obtained by irradiation of ultrasonic waves having a frequency of about 10 to about 70 KHz. However, a vibrator generating such low frequency waves is large in the size, and it is difficult to put such vibrator into the oral cavity to irradiate teeth with ultrasonic waves and assured attainment of effects cannot be expected in such case. However, if the device illustrated in the present embodiment is used, since the ultrasonic vibrator 13 is retained outside the oral cavity, its size is not particularly critical and it is possible to employ a vibrator capable of generating ultrasonic waves having a frequency of about 10 to 70 KHz without any particular disadvantage, with the result that an especially high treatment effect can be attained assuredly.

In an embodiment illustrated in FIGS. 7 to 14, a communicating passage communicating the inside portion 17 and outside portion 18 of the vessel with each other is formed, whereby breathing is made possible through not only the nose but also the oral cavity. Further, by formation of this communication passage, a saliva tube can optionally be laid out according to need. Accordingly, the treatment can be performed very easily without giving any pains to a patient. This embodiment will now be described in detail by reference to FIGS. 7 to 14.

Figure 7:
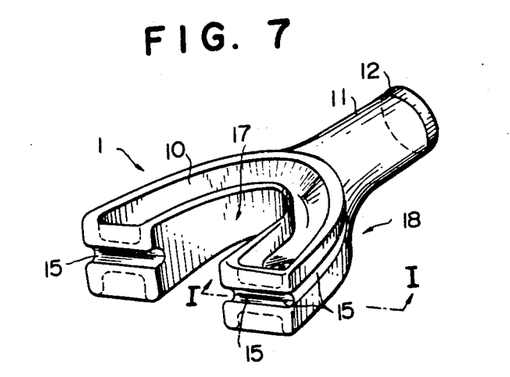
FIG. 7 is a perspective view illustrating an embodiment in which a communication passage is formed.

Referring now to FIG. 7, a groove 15 is formed as the communicating passage on the outer side face and top end face of a horseshoe portion 10 of a vessel 1. Examples of the section taken along the line II—II of FIG. 7 are shown in FIGS. 8 to 10.

Figure 8:
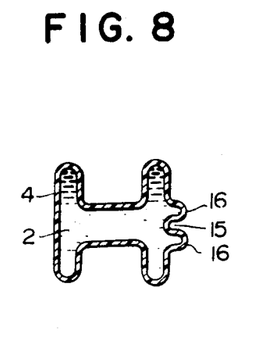

FIG. 8 illustrates an example in which a groove 15 is formed as the communicating passage. When the device is used for the treatment, the opened portion of the groove 15 falls in contact with the inner face of the cheek in the oral cavity. However, projections 16 are formed on both the sides of the groove 15 as clogging-preventing members to prevent clogging of the communicating passage 15. Accordingly, even during the treatment, the inside portion 17 of the vessel 1 is assuredly communicated with the outside portion 18 of the vessel 1 (see FIG. 7), and breathing is permissible through the oral cavity. The numbers and shapes of communicating passages 15 and projections 16 are not particularly critical but optional. It is possible to adopt an arrangement in which the thickness is increased in the vicinity of the communicating passage 15 to enhance the rigidity of the projections 16. The communication passage 15 of this example can be molded integrally with the tray from the same material, and hence, there is attained an advantage that the formation of the device is facilitated.

Figure 9:
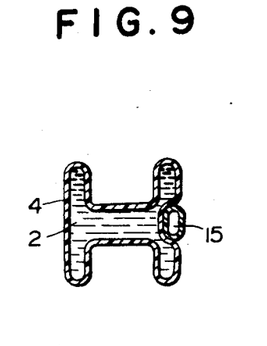

FIG. 9 illustrates an example in which a tube having a closed hollow portion is attached to form a communicating passage 15. The tube per se also acts as the clogging member. According to this example, there is attained an advantage that even if the communicating passage 15 is pressed considerably strongly in the oral cavity, it hardly is clogged.

Figure 10:
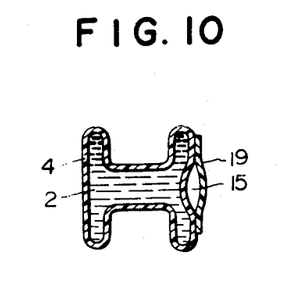

FIG. 10 illustrates an example in which a cover 19 acting as a clogging preventing member is spread on a part of the side face of the vessel 1 to form a communicating passage 15 between the vessel 1 and the enclosure 4.

Figure 11:
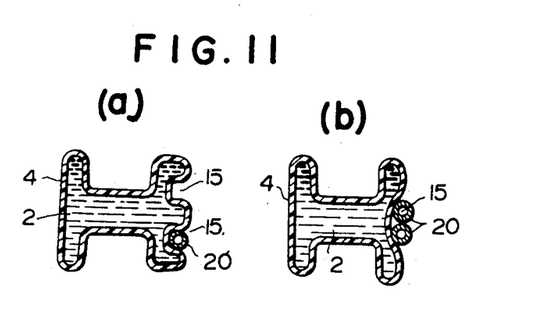
Figure 12:
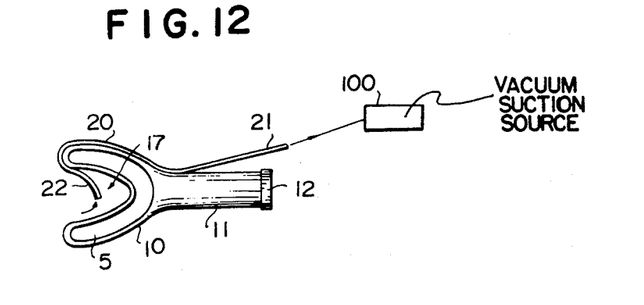
FIG. 12 is a plan view showing an arrangement of a saliva tube.

FIG. 11 illustrates examples in which two communicating passages 15 are formed and one of them is used for discharge of saliva. FIG. 11-(a) shows an example in which a saliva tube 20 is formed in one connecting passage 15, and FIG. 11-(b) illustrates an example in which one of the tubes in a saliva tube 20. As shown in FIG. 12, one end 21 of the saliva tube 20 is connected with a vacuum suction source 100, and the other end 22 is extended to the inner side portion 17 of the vessel 1 in the oral cavity and is opened at a place where saliva is stored. Instead of the above arrangement where two communicating passages 15 are especially formed, there may be adopted an arrangement in which one communicating passage 15 is formed on each of left and right branches of the horseshoe portion 10 and one of them is used for breathing while the other is used for discharge of saliva.

Figure 13:
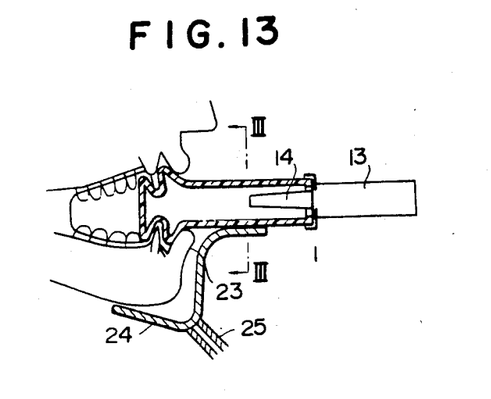
FIG. 13 is a sectional view showing the structure of a saliva receiver.
Figures 14, 15:
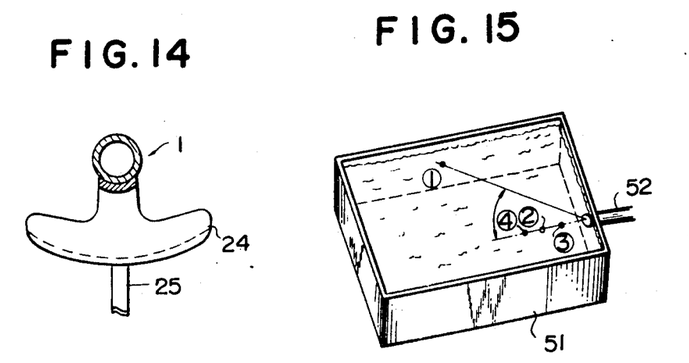
FIG. 14 is a view illustrating the section taken along the line III—III of FIG. 13.
FIG. 15 is a diagram illustrating Experiment 1.

FIGS. 13 and 14 illustrate and embodiment in which a saliva receiver 24 for receiving saliva discharged from the tooth rows in the oral cavity and overflown beyond the lower lip is attached to the vessel 1. Saliva stored in the receiver 24 is discharged through a tube 25.

By the following experiments made by us, it has been confirmed that even when a ultrasonic vibrator is located at a position relatively distant from a tooth to be treated, if a specific device such as the device of the present invention is used, ultrasonic waves generated by the vibrator can be effectively transmitted through a ultrasonic wave transmitting medium to the treatment position.

EXPERIMENT 1

As shown in FIG. 15, a horn 52 (29 KHz; the output was variable so that the amplitude of the top end could be arranged within a range of 0 to 20μ) of a ultrasonic vibrator was attached to a water tank 51 and degasified water was filled in the tank 51. Experiment point (1) was set on a line extending from the horn 52 in a direction inclined by 45° to the axial direction of the horn 52 so that the distance between the top end of the horn 52 and the experiment point (1) was 30 cm. Further, experiment points (3), (2) and (4) were set on a line extending from the horn 52 along the axial direction thereof so that the distances of the experiment points (3), (2) and (4) from the top end of the horn 52 were 5.5 cm, 7 cm and 8.5 cm, respectively. The horn 52 was oscillated and the sonic pressures at the respective points were measured. Supposed that the value of the sonic pressure at the top end of the horn 52 was 10, the values of sonic pressures at points (1), (4), (2) and (3) were 1.2, 1.2, 3.0 and 4–5, respectively. Namely, the point (1) distant by 30 cm from the top end of the horn 52 in a direction inclined by 45° to the axial direction of the horn 52 received the substantially same sonic pressure as that received by the point (4) distant only by 8.5 cm from the top end of the horn 52 and facing directly the horn 52. Thus, it was found that ultrasonic waves can be transmitted through degasified water as the transmitting medium without considerable attenuation.

A breaker filled with an 8 % aqueous solution of tin fluoride was set at each experiment point and an enamel sample (1.5 cm × 1.5 cm sample cut from a front tooth) was dipped and fixed in the aqueous solution in the beaker. Then, the sample was exposed to ultrasonic waves for 30 seconds. After the ultrasonic treatment, the sample was washed, brushed aand delimed at room temperature for 2 hours in an acetic acid buffer solution having a concentration of 0.1 mole/l, and the hardness of the sample was measured.

Figure 16:
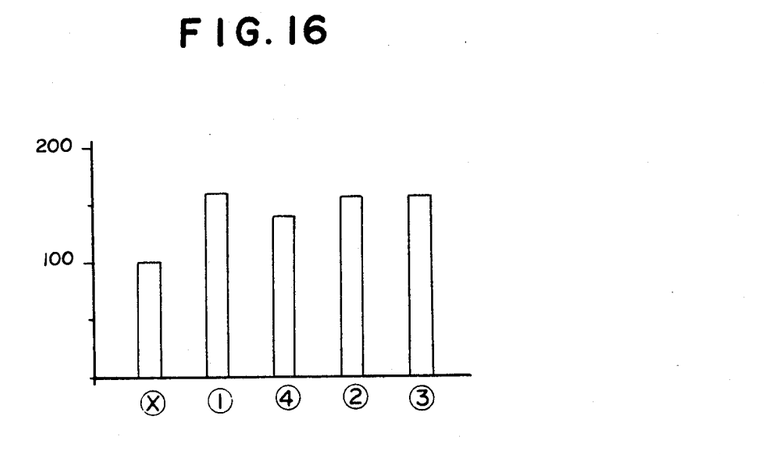
FIG. 16 is a graph illustrating results of Experiment 1.

Five samples were tested at each experiment point and the Vickers hardness was measured with respect to each sample. The average value is shown in FIG. 16. Similarly, the Vickers hardness was measured with respect to untreated 5 samples (only dipped in the tin fluoride solution for 30 seconds but not exposed to ultrasonic waves), and the obtained average value is shown in FIG. 16 [(X) in FIG. 16]. In samples exposed to ultrasonic waves the attained treatment effect was much higher than in the untreated samples. Among the treated samples, the treatment effect was not substantially different though the sonic waves received by the respective samples were different. It was confirmed that if the above-mentioned relative value of the sonic pressure is higher than about 1, a sufficient treatment effect can be attained.

EXPERIMENT 2

Figure 17:
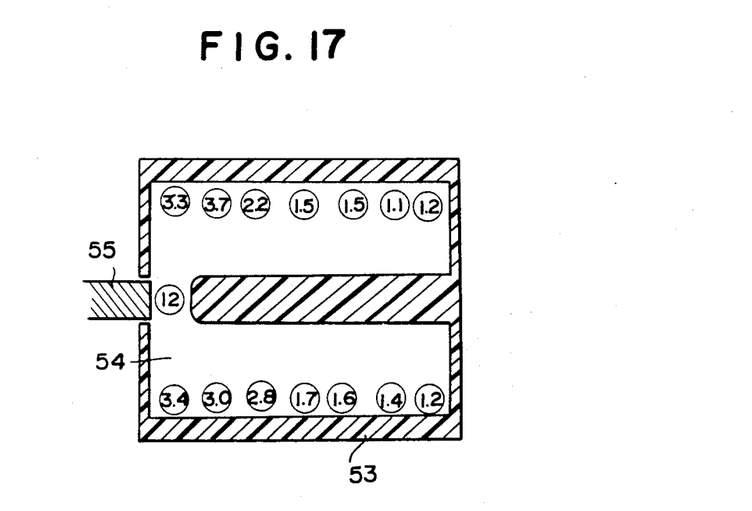
FIG. 17 is a diagram illustrating Experiment 2.

As shown in FIG. 17, a horseshoe groove 54 having the shape and size corresponding substantially to those of the tooth row was formed in a foamed styrol caselike vessel 53 having a size of about 6 cm × about 7 cm, and degasified water was filled in the groove 54 and a horn 55 (frequency = 29 KHz; amplitude = 10μ) was set to one end of the groove 54 and was oscillated. At points corresponding substantially to positions of respective teeth, sonic pressures were measured. The measured values are indicated by encircled numerical values in FIG. 17. From these results, it will readily be understood that a relative value of the sonic pressure is higher than 1.1 even at the point corresponding to the position of the grinding tooth, which is most distant from the horn 55, and ultrasonic waves capable of attaining a sufficient treatment effect can be transmitted to such remote point.

From the foregoing experiments, it was confirmed that the foregoing treatment effect can be attained by the use of a tooth decay-retarding treatment device comprising a vessel having a hollow portion capable of containing therein a ultrasonic wave transmitting medium, an enclosure surrounding this hollow portion and a groove to be in agreement with the tooth row, said enclosure being composed of a relatively soft material allowing transmission of ultrasonic waves but not allowing permeation of the ultrasonic wave transmitting medium, wherein if ultrasonic waves are given to a part of said vessel, they can be effectively transmitted to other parts of the vessel through said ultrasonic wave transmitting medium.

Thus, the device according to the invention is adapted to be disposed between a tooth decay-retarding agent contacted with the tooth surface and a ultrasonic vibrator for forming a reinforcing layer of the decay-retarding agent on the tooth surface by irradiation of ultrasonic waves, which includes a hollow portion for containing therein a ultrasonic wave transmitting medium and an enclosure surrounding said hollow portion, said enclosure being composed of a material allowing transmission of ultrasonic waves but not allowing permeation of the ultrasonic wave transmitting medium.

If this device is used, because of the presence of the ultrasonic wave transmitting medium in the hollow portion of the device, ultrasonic waves can be effectively transmitted to teeth over a relatively broad region. Moreover, ultrasonic waves can be effectively transmitted to teeth even when the ultrasonic wave vibrator is not held in the oral cavity. Accordingly, a ultrasonic wave generator of a relatively large size capable of generating ultrasonic waves of a low frequency suitable for the treatment can be used in the state disposed outside the oral cavity, and the treatment can be performed effectively without giving pains to a patient. Further, because of the presence of the ultrasonic wave transmitting medium-containing device intercened between the tooth surface and the ultrasonic vibrator, leakage or scattering of the tooth decay-retarding agent is effectively prevented during the treatment.

Thus, according to the invention the device has an enclosure means for enclosing an ultrasonic wave transmitting medium, this enclosure means including a sheet material which defines a hollow interior space for receiving the ultrasonic wave transmitting medium, and the sheet material has at least a portion which defines at the exterior of the sheet material a recess which is adapted to receive at least one tooth situated closely adjacent to the portion of the sheet material with a decay-retarding agent situated between and contacting the tooth and the sheet material, the sheet material having the property of being impermeable to the ultrasonic wave transmitting medium so that the latter cannot pass through the sheet material while the sheet material also has the property of transmitting ultrasonic waves from the medium in the interior of the enclosure means through the sheet material thereof to a tooth which is contacted by the decay-retarding agent.

It will be seen that an embodiment such as that of FIG. 7 has for its enclosure means a part adapted to be situated in close proximity to the teeth and having a substantially U-shaped configuration provided with a pair of legs which define between themselves an inner space while an outer space is situated at the exterior of this part of the enclosure means, and in FIG. 7 as well as FIGS. 8–11b there are shown various embodiments of communicating means situated at least in part along an exterior surface of the enclosure means to provide communication between the above inner and outer spaces.

Of course, in the embodiment of FIG. 3, the ultrasonic wave-generating means which includes the elements 9 is itself in the form of a hollow tray of a U-shaped cross section adapted to receive the enclosure means 1 of the invention. In FIG. 3 for the elements 9 it is possible to use electrostrictive vibrators composed of barium titanate porcelain or a lead zircotitanate porcelain (PZT), or a piezo-electric vibrator composed of quartz.. However, it is also possible to use a magnetostrictive vibrator. Thus, it is possible to provide for the vibrators 9 oscillation at an appropriate frequency to generate ultrasonic waves which are of course transmitted through the wall of the enclosure means 1 and the medium 2 therein so as to reach the teeth which are contacted by the agent 7 which also contacts the enclosure means 1.

As is apparent from FIG. 13, the member 24 forms a saliva-receiving means for receiving saliva and discharging the latter through the tube 25.

What is claimed is:

1. In a device for providing at the surface of at least one tooth a reinforcing layer of a decay-retarding agent, enclosure means for enclosing an ultrasonic wave transmitting medium, said enclosure means including a sheet material which defines a hollow interior space for receiving the ultrasonic wave transmitting medium, said sheet material having at least a portion which defines at the exterior of the sheet material a recess which is adapted to receive at least one tooth situated closely adjacent to said portion of the sheet material with a decay-retarding agent situated between and contacting the tooth and the sheet material, said sheet material having the property of being impermeable to the ultrasonic wave transmitting medium so that the latter cannot pass through the sheet material while said sheet material also has the property of transmitting ultrasonic waves from the medium in the interior of said enclosure means through the sheet material thereof to a tooth which is contacted by the decay-retarding agent, said enclosure means having a substantially U-shaped configuration provided by a pair of legs joined by a transverse portion of said enclosure means which is adapted to be situated at the front teeth, said enclosure means including an elongated tubular portion projecting outwardly from said transverse portion and terminating in a free end distant from said transverse portion, said tubular portion and U-shaped portion defining a common interior space for receiving the ultrasonic wave transmitting medium, and seal means situated at said free end of said tubular portion for sealing off the hollow space of said enclosure means.

2. The structure of claim 1 and wherein said recess is in the form of a groove for receiving one or more teeth.

3. The structure of claim 1 and wherein an ultrasonic wave transmitting medium is situated in the hollow interior space defined by said sheet material.

4. The combination of claim 3 and wherein said ultrasonic wave transmitting medium is in the form of a non-gaseous fluid.

5. The combination of claim 4 and wherein said ultrasonic wave transmitting medium is selected from the group consisting of silicone oils and degasified water.

6. The structure of claim 1 and wherein said sheet material is relatively soft and flexible.

7. The structure of claim 6 and wherein said sheet material of said enclosure means is selected from the group consisting of plastics, rubber, aluminum foil, and thin stainless steel.

8. The structure of claim 1 and wherein said recess has a substantially horseshoe-shaped configuration for receiving a row of teeth.

9. The combination of claim 1 and wherein said seal means includes a soft, flexible, at least partly elastic material having a self-restoring property.

10. The structure of claim 1 and wherein a saliva-receiving means is operatively connected with said enclosure means to be situated adjacent but at the exterior of the mouth of an individual for receiving saliva which discharges from the mouth.

11. The combination of claim 1 and wherein an ultrasonic wave generating means includes a horn adapted to extending through said seal means into the interior of said tubular portion for transmitting ultrasonic waves directly to a medium in the interior of said enclosure means with said seal means surrounding said horn to minimize escape of the ultrasonic wave transmitting medium at said free end of said tubular portion.

12. The combination of claim 1 and wherein said seal means has outer and inner portions with said outer portion of said seal means having a greater elasticity than said inner portion thereof.

13. The combination of claim 12 and wherein said outer portion of said seal means is made of a flexible film-like material selected from the group consisting of rubber, silicon rubber, saran, and polyvinyl alcohol, while said inner portion of said seal means is of a flexible, film-like material having some self-restoring property and selected from the group consisting of aluminum foil, natural and synthetic resins, and laminated materials composed of aluminum foil and synthetic resin, alumunim foil and paper, synthetic resin and paper, and any of the latter materials treated with wax.

14. In a device for providing at the surface of at least one tooth a reinforcing layer of a decay-retarding agent, enclosure means for enclosing an ultrasonic wave transmitting medium, said enclosure means including a sheet material which defines a hollow interior space for receiving the ultrasonic wave transmitting medium, said sheet material having at least a portion which defines at the exterior of the sheet material a recess which is adapted to receive at least one tooth situated closely adjacent to said portion of the sheet material with a decay-retarding agent situated between and contacting the tooth and the sheet material, said sheet material having the property of being impermeable to the ultrasonic wave transmitting medium so that the latter cannot pass through the sheet material while said sheet material also has the property of transmitting ultrasonic waves from the medium in the interior of said enclosure means through the sheet material thereof to a tooth which is contacted by the decay-retarding agent, said enclosure means having at a part which is adapted to be situated in close proximity to the teeth a substantially U-shaped configuration with said part of said enclosure means having a pair of legs respectively terminating in outer ends and defining between themselves an inner space while an outer space is situated at the exterior of said part of said enclosure means, said enclosure means having upper and lower surfaces adapted to be engaged by the lips, and communicating means situated at least in part along an exterior surface of said part of said enclosure means between said upper and lower surfaces thereof for providing communication between said inner and outer spaces, said communicating means being in the form of a wall portion of said sheet material which extends along at least one of said legs of said enclosure means at least from said outer end of said one leg to said outer space, and said wall portion being formed with a groove extending along said wall portion between said upper and lower surfaces of said enclosure means at least from said outer end of said one leg along a part of said wall portion which communicates with said outer space, so that through said groove communication is provided between said inner and outer spaces.

15. The combination of claim 14 and wherein said communicating means includes a means for preventing clogging of communication between said inner and outer spaces.

* * * * *